US012622710B2

(12) United States Patent
Bosch et al.

(10) Patent No.: US 12,622,710 B2
(45) Date of Patent: May 12, 2026

(54) CENTER OF ROTATION GUIDE

(71) Applicant: ARTHREX, INC., Naples, FL (US)

(72) Inventors: Stephan M. Bosch, Naples, FL (US);
Allen E. Holowecky, Naples, FL (US);
Steven J. Lee, Scarsdale, NY (US);
Steven S. Shin, Los Angeles, CA (US);
Michael J. Garcia, Tampa, FL (US);
Damon C. Adamany, Peoria, AZ (US)

(73) Assignee: ARTHREX, INC., Naples, FL (US)

( * ) Notice: Subject to any disclaimer, the term of this
patent is extended or adjusted under 35
U.S.C. 154(b) by 226 days.

(21) Appl. No.: 18/356,268

(22) Filed: Jul. 21, 2023

(65) Prior Publication Data

US 2025/0025187 A1      Jan. 23, 2025

(51) Int. Cl.
*A61B 17/17*          (2006.01)
*A61B 17/04*          (2006.01)

(52) U.S. Cl.
CPC ...... *A61B 17/1739* (2013.01); *A61B 17/0401*
(2013.01); *A61B 17/1796* (2013.01); *A61B
17/1728* (2013.01)

(58) Field of Classification Search
CPC ............ A61B 17/1796; A61B 17/1728; A61B
17/1703; A61B 2090/103; A61B 17/1714;
A61B 17/1778; A61B 17/1782; A61B
17/171; A61B 17/39; A61F 2/0805
See application file for complete search history.

(56) References Cited

U.S. PATENT DOCUMENTS

| | | | |
|---|---|---|---|
| 8,608,741 | B2 | 12/2013 | Orbay et al. |
| 9,603,625 | B2 | 3/2017 | Orbay et al. |
| 2005/0043806 | A1 | 2/2005 | Cook et al. |
| 2007/0073408 | A1 | 3/2007 | Acker et al. |

(Continued)

FOREIGN PATENT DOCUMENTS

CA          2772915 C      9/2017

OTHER PUBLICATIONS

International Search Report and Written Opinion for International
Application No. PCT/US2024/037529 dated Oct. 4, 2024.

(Continued)

*Primary Examiner* — Matthew J Lawson
(74) *Attorney, Agent, or Firm* — Potomac Law Group,
PLLC

(57)          ABSTRACT

Surgical constructs, assemblies and methods of elbow repair
and reconstruction. A center of rotation guide has specific
dimensions configured to be secured on either the lateral or
medial side of the elbow. At one end, the guide is provided
with a plurality of full concentric through-holes (circles of
different diameters) with bisecting lines every 90 degrees to
identify the center of rotation on the lateral and medial
epicondyle. At another end, the guide is provided with a
linear pattern of through-holes or apertures located about the
centerline of the guide. The linear pattern of through-holes
identifies the attachment point on the ulnar tuberosity. The
concentric and linear pattern through-holes of the guide are
sized to receive instrumentation such as K-wire guides (Continued)

and/or drill guides. One or more spikes or tines are provided on the bottom of the guide for stabilization during use.

18 Claims, 5 Drawing Sheets

(56)                    References Cited

U.S. PATENT DOCUMENTS

| | | | |
|---|---|---|---|
| 2009/0228017 A1* | 9/2009 | Collins .............. | A61B 17/1739 |
| | | | 623/13.14 |
| 2013/0131681 A1 | 5/2013 | Katrana et al. | |
| 2013/0197523 A1* | 8/2013 | Fitzpatrick ......... | A61B 17/1778 |
| | | | 606/80 |
| 2023/0233217 A1* | 7/2023 | Miller .................. | A61N 1/0539 |
| | | | 606/96 |
| 2024/0252180 A1* | 8/2024 | Khan .................. | A61B 17/151 |
| 2025/0082367 A1* | 3/2025 | Bell .................. | A61B 17/8897 |

OTHER PUBLICATIONS

Orbay., "Surgical Technique Guide IJS-Elbow elbow stabilization system", Skeletal Dynamics, Miami, FL, 20 pages, Jul. 2020.

* cited by examiner

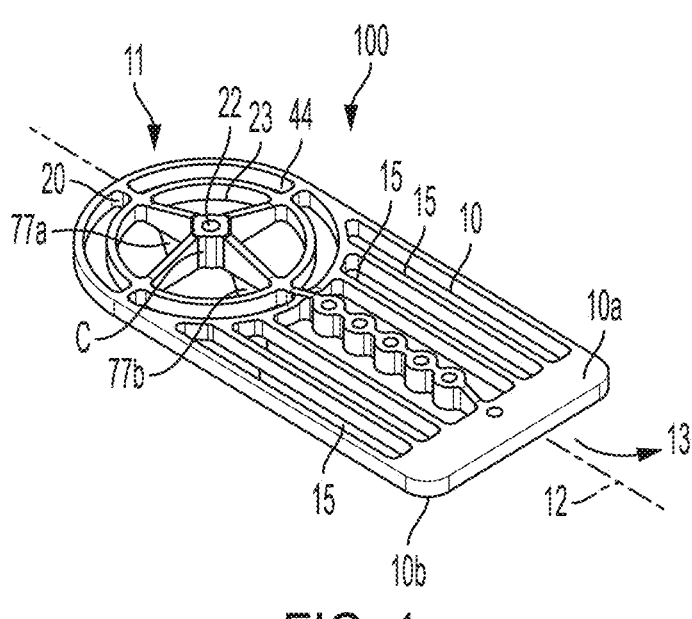
FIG. 1
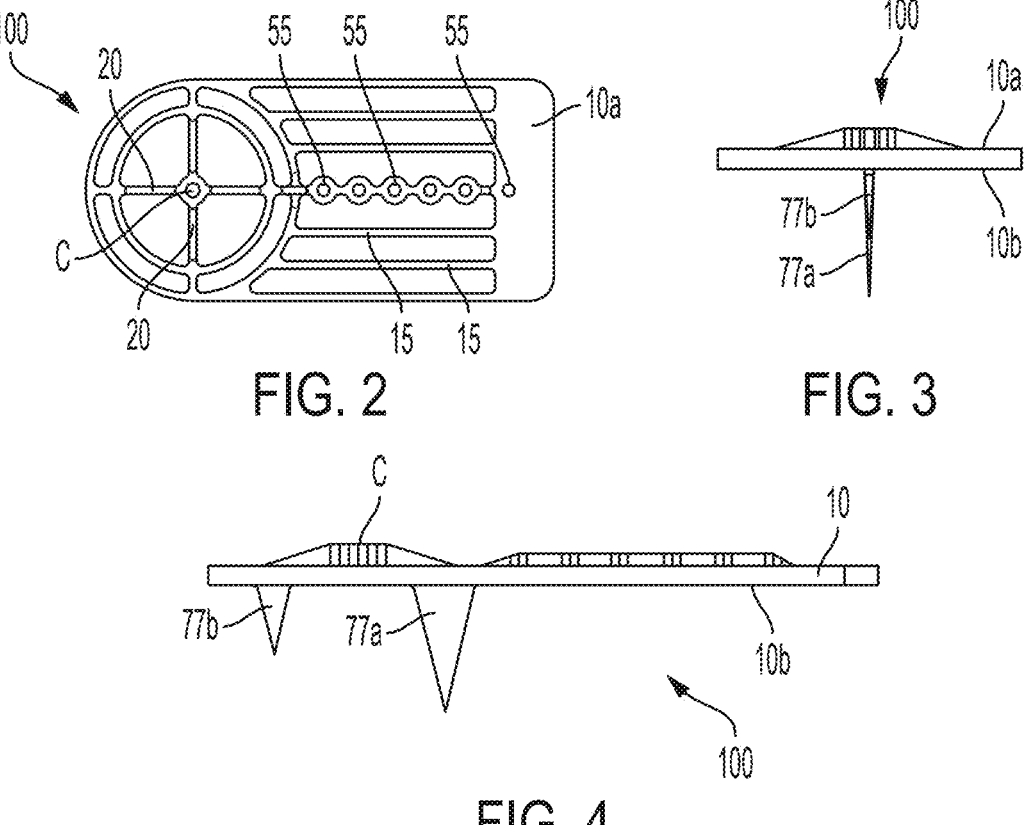
FIG. 2
FIG. 3
FIG. 4

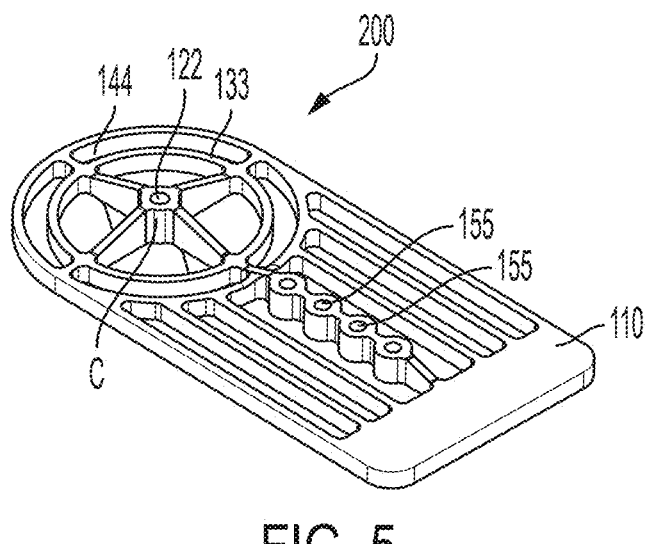
FIG. 5
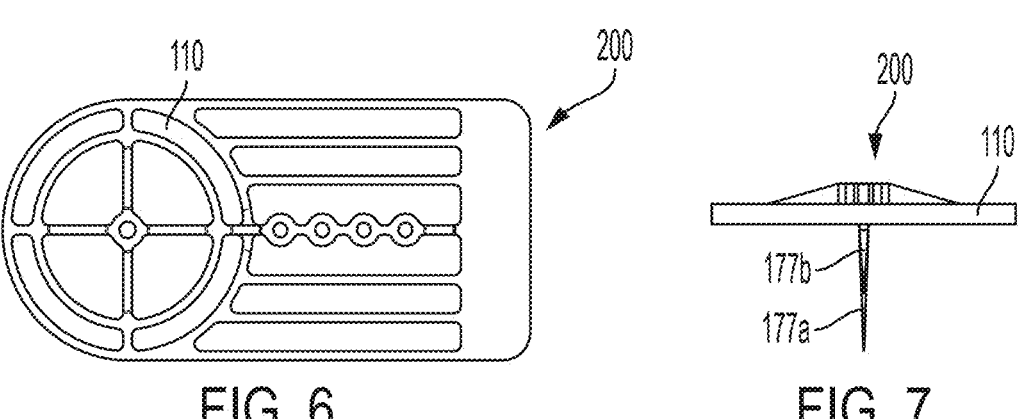
FIG. 6
FIG. 7
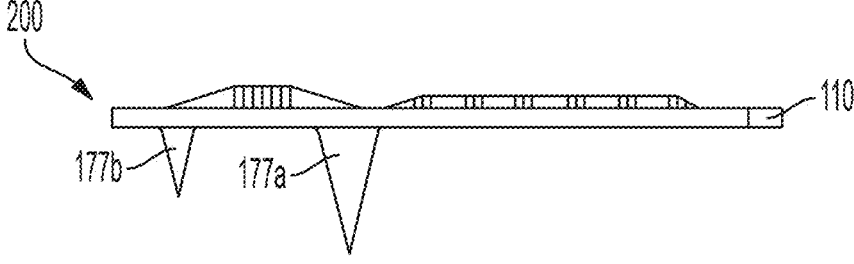
FIG. 8

CENTER OF ROTATION GUIDE

BACKGROUND

The disclosure relates to the field of surgery and, more particularly, to guides for determining a center of rotation of an elbow joint and associated methods of surgical repairs.

SUMMARY

A center of rotation guide is in the form of a cuboid with specific dimensions configured to be secured on either the lateral or medial side of the elbow. At one end, the guide is provided with a plurality of full concentric through-holes (circles of different diameters) with bisecting lines about every 90 degrees to identify the center of rotation on the lateral or medial epicondyle. At another end, the guide is provided with a linear pattern of through-holes or apertures located about the centerline of the guide. The linear pattern of through-holes identifies the attachment point on ulna.

The concentric and linear pattern through-holes of the guide are sized to receive instrumentation such as K-wires, guides and/or drills. One or more bone engaging structures (spikes or tines) can be provided on one of the surfaces of the guide for stabilization during use.

Methods of surgeries are also disclosed. In an embodiment, collateral ligament repair or reconstruction is conducted with a guide configured to accurately identify the center of rotation of the lateral and/or medial epicondyle for medial/lateral collateral ligament repair/reconstruction around the elbow.

BRIEF DESCRIPTION OF THE DRAWINGS

FIG. 1 illustrates a perspective view of a center of rotation guide.

FIG. 2 is a top view of the guide of FIG. 1.

FIG. 3 is a lateral side view of the guide of FIG. 1.

FIG. 4 is a front view of the guide of FIG. 1.

FIG. 5 illustrates a perspective view of another center of rotation guide.

FIG. 6 is a top view of the guide of FIG. 5.

FIG. 7 is a lateral side view of the guide of FIG. 5.

FIG. 8 is a front view of the guide of FIG. 5.

DETAILED DESCRIPTION

Figure 9:
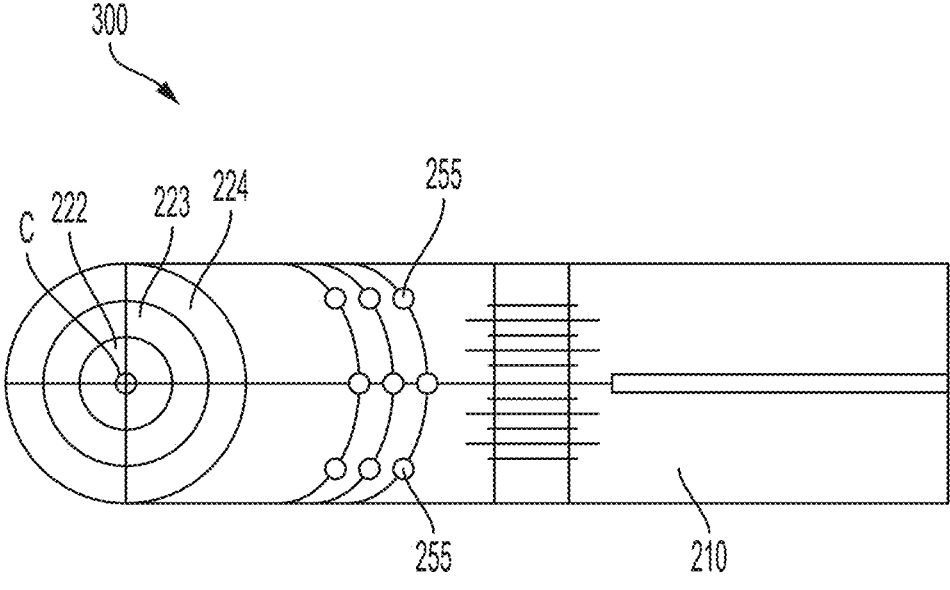
FIG. 9 illustrates a top view of another center of rotation guide.

The disclosure provides surgical constructs, assemblies, kits, and methods for locating, determining, and marking the center of rotation of the elbow joint (i.e., center of rotation of the lateral and/or medial epicondyle) for repairs and reconstructions of the elbow, for example, ulnar collateral ligament (UCL) repair or lateral ulnar collateral ligament (LUCL) repair.

The surgical guide of the present disclosure allows finding the center of rotation in a quick, easy, and efficient manner. The surgical guide eliminates the need for the current use of radiographic or fluoroscopic images, or the use of 3-dimensional computed tomography (CT), that currently aid surgeons in finding the center of rotation. Radiography, fluorography, and CT are time consuming, difficult, and expose both the providers and patients to radiation, while still averaging about 1.1 mm of elongation throughout the elbow's range of motion. Fluoroscopy is also associated with substantial rotational errors and large inconsistencies among surgeons.

As detailed below, the surgical guide of the disclosure assists surgeons in locating the center of rotation via three checks:

1. using the outer edge of the capitellum articular surface and the equidistant central point from the edge (for the lateral collateral ligament);

2. using the convergent point of the bisecting lines of the radial head measured at various degrees such as 0, 45 and 90 degrees; and 3. using the drill hole pattern that, when combined with k-wire(s), can determine if the isometric location has been found when the elbow is put through the range of motion.

The use of the guide eliminates the need for fluoroscopy, radiography, and CT; speeds up the procedure time; eliminates exposure to radiation; improves surgeons' accuracy; and improves the elbow isometry in collateral ligament repair/reconstruction. The use of the guide also eliminates the need for finding the true axis of rotation (and the use of a corresponding axis guide and subsequent second surgery for removal) as commonly used in current elbow stabilization systems.

As detailed below, a center of rotation guide can include a solid metal body in the shape of a general cuboid having a length of about 1.9 to about 2.25 inches, a width of about 0.8 to about 1.2 inches, and a height of about 0.06 to 0.12 inches. One end of the guide has a semi-circular configuration and is provided with two or more concentric through-holes or circles, which pinpoint the center of rotation. The other end of the guide has a generally rectangular shape and is provided with a plurality of through-holes or apertures. The plurality of through-holes or apertures can form a linear pattern located about the centerline of the guide. The linear pattern of through-holes or apertures helps in identifying the attachment point on the ulnar tuberosity. One or more bone engaging structures (spikes or tines) can be provided on one of the surfaces of the guide (on the bottom of the guide) for stabilization during use.

The concentric through holes and the plurality of linear through-holes or apertures are configured and sized to engage one or more instruments and/or devices (such as K-wires, drills etc.) and to allow easy passage of fixation devices (such as screws, suture-button constructs, suture anchors, etc.) and flexible members (such as flexible strands, for example, sutures and/or suture tapes) associated with fixation devices used for elbow reconstruction (such as graft fixation).

Methods of determining a center of rotation of elbow as well as methods of elbow reconstructive surgeries are also disclosed. An exemplary method includes inter alia the steps of: (i) positioning a center of rotation guide on a medial or lateral side of the elbow; and (ii) securing a surgical instrument to the guide. The method can further include the steps of identifying the center of rotation of the elbow; engaging a plurality of bone engaging structures (spikes or tines) located on the bottom of the guide with one or more bone surfaces/edges of the bone; and drilling into elbow. The method can further include the step of attaching a graft to the elbow bone(s); and securing the graft with one or more fixation devices.

Figure 10:
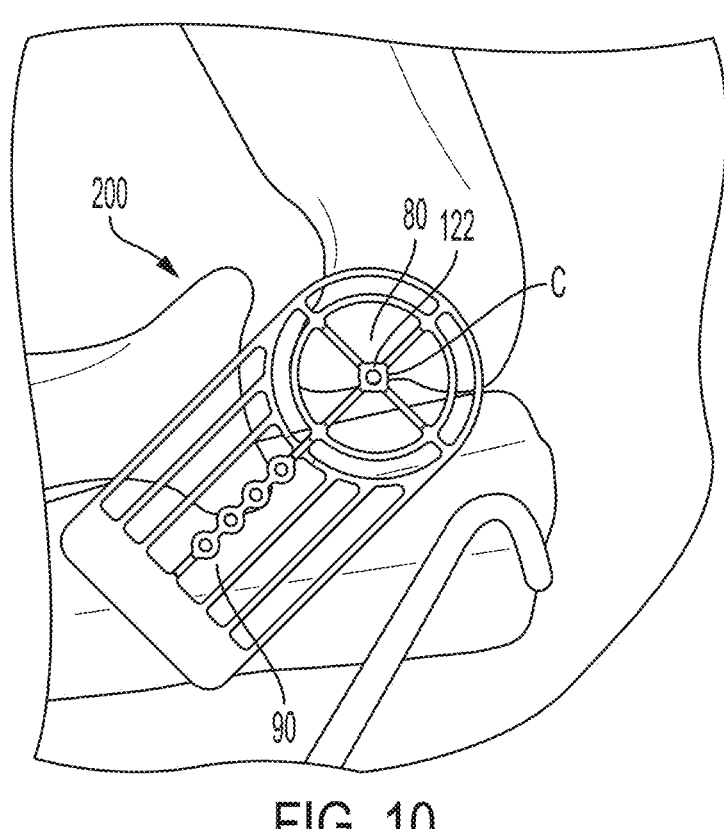
FIGS. 10-12 illustrate subsequent steps of reconstructive surgery with a center of rotation guide.
Figure 11:
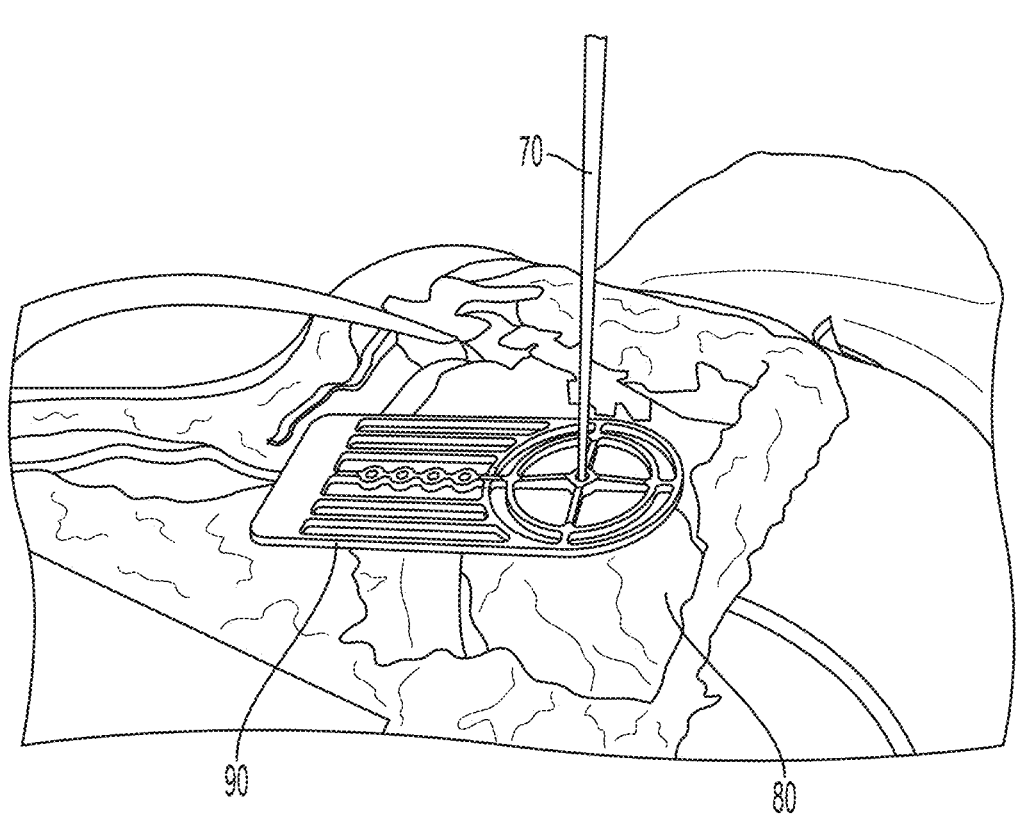
Figure 12:
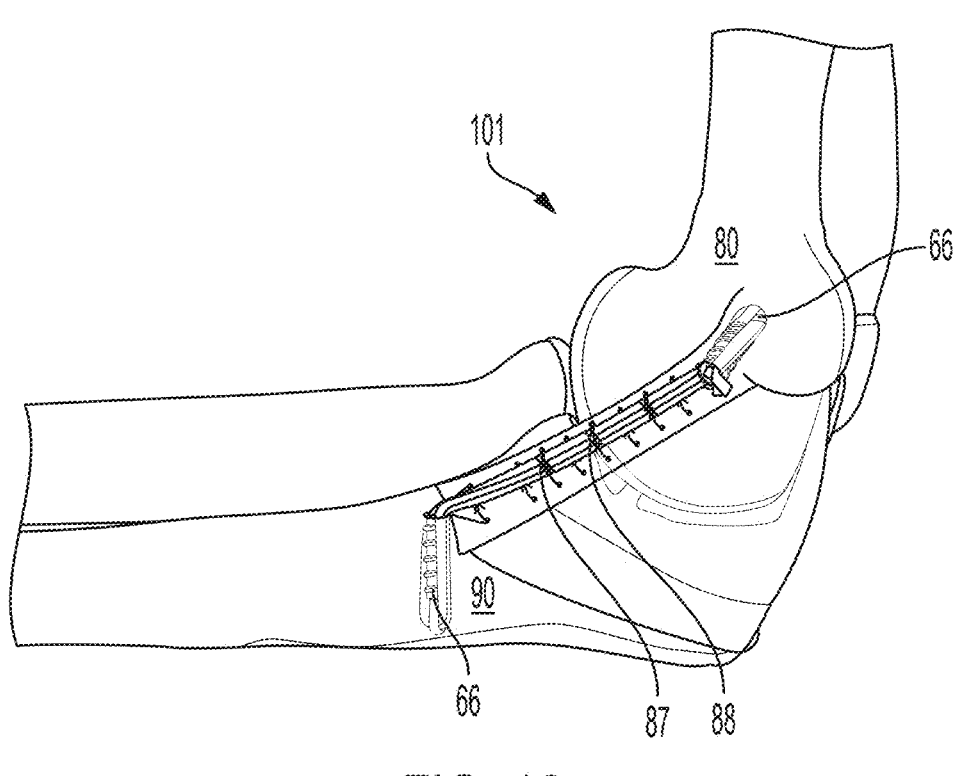

Referring now to the drawings, where like elements are designated by like reference numerals, FIGS. 1-9 illustrate various views of exemplary center of rotation guide 100, 200, 300 (guide 100, 200, 300; elbow guide 100, 200, 300;

construct 100, 200, 300; surgical construct 100, 200, 300; jig 100, 200, 300). FIGS. 10-12 illustrate steps of an exemplary method of reconstructive surgery with a center of rotation guide.

Center of rotation guide 100 of FIGS. 1-4 comprises a body 10 having a general overall cuboid shape, i.e., a three-dimensional solid body with about six sides or faces (facets) that are all positioned at about 90 degrees angles relative to each other. In an exemplary embodiment, body 10 of guide 100 is a cuboid block with a length L, a width W, a height H. Length L can be of about 1.9 to about 2.25 inches; width W can be of about 0.8 to about 1.2 inches (0.9 inches), and height H can be of about 0.060 to 0.120 inches, dimensions which allow the guide to be contained to the elbow, as detailed below. In an exemplary embodiment, center of rotation guide 100 can have a length of about 1.98 inches and a width of about 0.9 inches.

As shown in FIG. 1, an end of the guide 100, for example end 11, has a semi-circular configuration and is provided with two or more concentric through-holes or circles which locate/indicate the center of rotation C. In an exemplary only embodiment, end 11 is provided with three concentric through-holes 22, 33, 44 or circles 22, 33, 44, which pinpoint the center of rotation C. Another end of the guide 100, for example end 13, is generally rectangular and is provided with a plurality of through-holes 55 or apertures 55. The plurality of through-holes 55 or apertures 55 can form a linear pattern located about the centerline 12 of the guide 100. The linear pattern of through-holes 55 or apertures 55 helps in identifying the attachment point on the ulnar tuberosity. One or more bone engaging structures 77a, 77b (spikes 77a, 77b or tines 77a, 77b) can be provided on one of the surfaces of the guide (for example, on bottom surface 10b of the guide 100, as shown in FIG. 4) for stabilization during use. The spikes or tines can have similar or different configurations and/or dimensions.

The concentric through-holes 22, 33, 44 and the plurality of linear through-holes 55 or apertures 55 are configured and sized to engage one or more surgical instruments or devices (such as K-wires, pins, drills etc.) and to allow easy passage of fixation devices (such as screws, suture-button constructs, suture anchors, etc.) and flexible members (such as flexible strands, for example, sutures and/or suture tapes) associated with fixation devices used for elbow reconstruction (such as graft fixation), as detailed below.

The concentric through-holes 22, 33, 44 extend from a first surface or side 10a of the body 10 to a second, opposite surface or side 10b of the body 10. The concentric through-holes 22, 33, 44 are configured to allow engagement with, and passage of, one or more instruments, for example, drills or any cutting instruments during a drilling procedure. Concentric through-holes 22, 33, 44 include a plurality of bisecting lines 20 about every 90 degrees to identify the center of rotation C on the lateral and/or medial epicondyle. Concentric through-holes 22, 33, 44 can be open ended bores (for example, cylindrically shaped and longitudinally extending) provided about parallel to each other and for receiving one or more instruments (for example, a drill guide and/or a drill) during use. Concentric through-holes 22, 33, 44 can be provided with chamfered edges. Concentric through-holes 22, 33, 44 can be symmetrically located relative to center C of the cuboid body. At least one or all of concentric through-holes 22, 33, 44 can have internal threading for receiving one or more instruments. The concentric through-holes 22, 33, 44 are provided as circles to overlay on the capitellum. Central hole 22 is dimensioned big enough to fit a pin for a fixation device (for example, a suture anchor such as an Arthrex SwiveLock® anchor).

The plurality of through-holes 55 or apertures 55 identify the attachment point on the ulnar tuberosity. In an exemplary embodiment, six through-holes 55 are provided symmetrically located to each other and along the longitudinal axis 12. The linear 6× hole pattern identifies the attachment point on the supinator crest (for LUCL repair/reconstruction) or sublime tubercle (for UCL repair/reconstruction). When used with K-wires, the elbow can be put through its range of motion to perform a check before drilling bone tunnels for fixation devices (such as suture anchors). Parallel lines 15 are provided on each side of the through-holes 55 and along the body 10 with dimensions about the size of the radial head, with an open slot on the opposite side. In use, the middle of the radial head points to the center of rotation C at different angles of elbow flexion. Using a marking pen, the surgeon can draw multiple lines on the capitellum at different angle of elbow ROM, and the point where those lines bisect corresponds to the center of rotation C.

One or more bone engaging structures 77a. 77b (spikes 77a, 77b; tines 77a, 77b points 77a. 77b; barbs 77a, 77b;) can be provided on one of the surfaces of the guide (for example, on bottom surface 10b of the guide 100, as shown in FIG. 4) for stabilization during use. In one embodiment, two spikes or tines 77a, 77b are provided on the underside 10b of the guide 100, at about 0.254 inches from center C. The two spikes can have similar or different dimensions and/or configurations. The two spikes can be formed of same or different material as the one of the body 10, and can be formed integral with the body 10 or separately from it. In an embodiment, proximal tine 77b has a length smaller than the length of distal tine 77a. In an embodiment, proximal tine 77b is of about 5 mm in length, and distal tine 77a is of about 9 mm in length.

Guide 100 can be manufactured from metals, metal alloys, non-metals, plastics, or combinations thereof. Guide 100 can be a metal guide produced by 3D printing, injection molding, or machining. Guide 100 can be formed of stainless steel; can be disposable; can be reusable. Guide 100 is a simple construct that allows precise, accurate and convenient positioning on an anterior face of a bone to be grafted/repaired/reconstructed (e.g., the lateral or medial side of the elbow).

Reference is now made to FIGS. 5-8 which illustrate another exemplary embodiment. Center of rotation guide 200 is about similar to center of rotation guide 100 described above, in that it is also provided with a body 110 with three concentric through-holes 122, 133, 144, which pinpoint the center of rotation C. End 113 of guide 200 is provided with four through-holes 155 or apertures 155 that form a linear pattern located about the centerline of the guide 200. The dimensions of the bone engaging structures 177a, 177b (spikes or tines 177a, 177b) are also smaller than those of guide 100.

FIG. 9 illustrates center of rotation guide 300 which is about similar to guides 100, 200 described above in that it is also provided with a body 210 with three concentric through-holes 222, 233, 244, which pinpoint the center of rotation C. However, guide 300 includes three layers, each with three through-holes 255 that are in a concentric equidistance from the center of rotation hole 222 (COR hole). These holes 255 are provided for at least two reasons: if the surgeon wants to make a two-limb construct, the surgeon can use these holes so that there is 1 hole in the COR and 2 holes on the ulna, making a V-shaped construct. This distance needs to be measured to correspond to the average distance from the COR to about the level of the proximal articular surface of the radial head. Also, these holes 255 can be used to help confirm the COR is accurate: the surgeon can put a marking pen dot in the holes and put the elbow into a ROM and the surgeon should see the dots going through the hole through the ROM. The V construct can have the one limb tensioned at around 30 degrees of flexion and the other at about 60 degrees of flexion.

Center of rotation guides 100, 200, 300 detailed above can be manufactured from metals, metal alloys, non-metals, plastics, or combinations thereof. A center of rotation guide 100, 200, 300 can be a metal guide produced by 3D printing, injection molding, or machining. A center of rotation guide 100, 200, 300 can be formed of stainless steel. A center of rotation guide 100, 200, 300 can be disposable. A center of rotation guide 100, 200, 300 can be reusable. Guide 100, 200, 300 is a simple construct that allows precise, accurate and convenient positioning on an anterior face of a bone to be grafted (e.g., the lateral or medial side of the elbow). Guide 100, 200, 300 can be also contoured since the lateral epicondyle and the supinator crest of the ulna are not in the same plan.

Guide 100, 200, 300 has applicability to various open procedures, with particular application to ulnar collateral ligament (UCL) and lateral ulnar collateral ligament (LUCL) repairs and reconstructions. Although guides 100, 200, 300 have been described above with reference to particular embodiments having a liner pattern of six or four through-holes, it must be understood that the disclosure is not limited to these specific-only embodiments. Thus, the present disclosure contemplates guides with three, four, five, six and even more inline through-holes (of similar or different diameters) for precisely identifying attachment to the ulnar tuberosity and checking isometry.

For example, a guide with an additional hole at the end of the guide (in addition to the 6× linear pattern) would provide two additional holes at the end of the guide, wherein in the one of the two additional holes a surgeon could position another drill hole in the supinator crest of the ulna. The surgeon could easily check isometry in real time leaving a guidewire in the center of rotation (COR) of the humerus, then drilling a hole in one of the last two holes, and then putting the elbow through a ROM, and seeing if the hole that was drilled matches with the hole in the center of rotation guide.

Reference is now made to FIGS. 10-12 which illustrate steps of a method of elbow repair with guide 100, 200, 300 of the present disclosure, specifically, an elbow UCL with InternalBrace™ (medial side) repair 101 (FIG. 12). FIG. 10 illustrates exemplary guide 200 of FIG. 5 positioned on elbow. The concentric through-holes 122, 133, 144 are provided as circles to overlay on capitellum 80. The linear through-holes 155 identify the attachment point on the ulnar tuberosity 90.

FIG. 11 illustrates a surgical assembly with exemplary guide 200 and associated driver 70. Guide 200 can be provided for both lateral and medial ulna, depending on the intended application and surgical needs. Central hole 122 is dimensioned big enough to fit a pin and/or driver 70 for a fixation device 66 (for example, a suture anchor 66 such as an Arthrex SwiveLock® anchor 66).

FIG. 12 illustrates an elbow UCL repair with UCL InternalBrace™ repair 101 with exemplary guide 200 placed on the capitellum 80 and ulnar tuberosity 90. Placement on the capitellum 80 and ulnar tuberosity 90 and determining the center of rotation C is conducted by surgeon with a center of rotation guide (such as guide 100, 200, 300). The outer edge of the articular surface of capitellum 80 is aligned with the semicircular edge of the body 10, 110, 210 of the guide 100, 200, 300 and the equidistant central point from the edge. Using the convergent point of the bisecting lines of the radial head measured at various degrees such as 0, 45 and 90 degrees, the surgeon determines the center of rotation C (and can mark it with a marking pen, for example).

The linear pattern of through-holes 55, 155, 255 is placed on the supinator crest (for LUCL repair) or the sublime tubercle (for UCL repair) of the ulnar tuberosity. Using one through-hole of the linear pattern of through-holes 55, 155, 255, the surgeon determines the attachment on the ulnar tuberosity (sublime tubercle for UCL repair) (i.e., the surgeon introduces the K-wire in one or any of the through-holes 55, 155, 255 to determine the ideal point of attachment). When combined with k-wire(s), the surgeon can determine if the isometric location has been found when the elbow is put through the range of motion.

An anchor drill guide is inserted into hole 22, 122, 222 on the capitellum 80. A socket is drilled in the supinator crest for placement of a fixation device. An exemplary suture anchor 66 such as an Arthrex SwiveLock® anchor loaded with a suture tape 88 (for example, FiberTape® suture tape 88) is inserted into ulna until the anchor is flush with the bone. The native ligament can be repaired back to the supinator crest of the ulnar tuberosity using flexible strand 87 (for example, suture 87).

A drill guide is placed on the medial epicondyle (at the determined center of rotation C) and a socket is drilled for placement of another fixation device 66, such as another suture anchor 66 (for example, an Arthrex SwiveLock® anchor 66). The tails of the suture tape 88 are loaded onto the suture anchor 66 and the loaded anchor is inserted and secured into the bone socket.

Various fixation devices in the form of screws, buttons, suture-button constructs, anchors, soft suture anchors (such as knotted and knotless suture anchors) and plates, among many others, can be employed with center of rotation guide 100, 200, 300.

Fixation device 66 can be made of one or more pieces or can be provided as an integrated device. In an exemplary embodiment, fixation device 66 is a Corkscrew® anchor. In an exemplary embodiment, fixation device 66 is a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein. An exemplary knotless fixation device 66 can comprise an anchor body (or screw) and an eyelet.

Fixation device 66 can be also in the form of a soft anchor (soft suture anchor, or all-suture soft knotless anchor) provided with a soft anchor sleeve (sheath or tubular member) with two open ends, and at least one flexible coupler extending through the soft anchor sleeve (sheath) and with limbs each exiting an open end of the sheath. The flexible couplers may extend through the sleeve in similar or different directions and/or orientations and/or locations. Details of an exemplary soft suture anchor with a soft anchor sleeve (sheath or tubular member) and flexible shuttling strands are set forth, for example, in U.S. Pat. No. 10,849,734 issued Dec. 1, 2020, entitled "Methods of Tissue Repairs," the disclosure of which is incorporated by reference in its entirety herein.

Flexible strands 87, 88 can be formed of any flexible material such as suture or tape, or combination of suture and tape. The suture may be in the form of any known suture construct, such as multifilament, braided, knitted, woven suture, elastic suture, or including fibers of ultrahigh molecular weight polyethylene (UHMWPE) or the Fiber-Wire® suture (disclosed in U.S. Pat. No. 6,716,234, the disclosure of which is hereby incorporated by reference in its entirety herein). The tape may be formed of suture tape, for example, Arthrex FiberTape®, which is a high strength suture tape that is braided and rectangular-like in cross section and as disclosed in U.S. Pat. No. 7,892,256, the disclosure of which is hereby incorporated by reference in its entirety herein.

Flexible strands 87, 88 can be any couplers in the form of elongated members, fibers, or materials, or combinations thereof. Flexible strands 87, 88 can include a single filament, or fiber, or can include multiple continuous filaments, segments or regions of filaments that have different configurations (for example, different diameters and/or different compositions). The filament regions/segments can each be homogenous (i.e., formed of same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

Center of rotation guides 100, 200, 300 described above can be included in a surgical kit, assembly, or system to simplify the surgeon's task of selecting a specific instrument and to aid in the overall surgical procedure. A surgical kit for an open elbow surgical repair can include one or more guides 100, 200, 300 and at least one other surgical instrument or device for use with the guide(s) 100, 200, 300. The surgical kit can include awls or equivalent devices, as well as drills or bone-penetrating devices. The surgical kit can also include a tensioner and/or bone plates and associated instrumentation. The surgical kit can include fixation devices (such as anchors 66, screws, suture-button constructs plates, etc.) and flexible members (such as sutures 87 and suture tapes 88) to be employed in conjunction with the bone tunnels, bores or holes formed with and by the guide 100, 200, 300.

Methods of determining an elbow center of rotation and methods of associated elbow surgery are also disclosed. An exemplary method includes inter alia the steps of: (i) positioning a center of rotation guide 100, 200, 300 on a medial or lateral side of the elbow; and (ii) determining the center of rotation of the elbow. The method can further include the steps of: securing the center of rotation guide 100, 200, 300 on the capitellum 80 so that a semicircular end of the guide 100, 200, 300 is aligned with an outer edge of the articular surface of the capitellum 80; engaging a plurality of spikes 77a. 77b or tines located on a bottom of the guide 100, 200, 300 to the articular the surface of the capitellum; securing a cutting instrument 70 to the guide 100, 200, 300; and drilling into the elbow.

The guide 100, 200, 300 described above helps find confirm isometry of a repair/internal brace/reconstruction by three different methods: 1) finding the Center of Rotation (CoR) on the humerus—this is the most effective and reliable way of doing this by using the concentric circles on the guide 100, 200, 300, and utilizing the central hole of those concentric circles. This is the most accurate way to find the CoR; 2) The CoR coincides with where the center of the Radial Head points at the Capitellum at two different angles—the surgeon takes where they bisect (one can do it, for example, at 30 degrees and 90 degrees), so the surgeon can opt to use this option as well as, or instead of, the Concentric circle method. Thus, the lines that are on the guide help to frame the Radial head, and the surgeon can mark out those lines and where they bisect should coincide with the CoR. 3) The multiple in-line holes on the guide 100, 200, 300 confirm isometry and help select a spot on the ulna on the Supinator Crest. While the drill hole spot on the ulna does not matter in terms of isometry, a surgeon can put it in line with the Radio-capitellar joint, partly because the LUCL partly attaches there, and also because if it is placed any more distally (which the LUCL does attach distally as well), the graft/InternalBrace™ ligament can rub on the Radial head throughout the elbow ROM. With the multiple holes, after putting in the guidewire in the Concentric hole, the surgeon can then pick one of the multiple in-line holes to drill a hole that corresponds with the midpoint between the anterior and posterior cortices on the ulna that is in line with the R-C joint and drill the hole. After drilling the hole, the surgeon can put the elbow through a range of motion, and that the hole drilled in the bone will be within 1.1 mm (or less) of the hole in the guide. Because of the tines on the CoR guide, the surgeon would have to pull the guide off of the bone to check this isometry. If because the tines are of different lengths and makes looking through the drill holes unconventional because of the tilt, the surgeon can just flip the guide over to see it better that way.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A center of rotation guide comprising:
   a cuboid body with a length, a width and a height;
   at least one protuberance adapted to engage a surface of a capitellum of an elbow;
   two or more concentric circular holes of different diameters, the two or more concentric circular holes being positioned at one end of the cuboid body; and
   a linear pattern of a plurality of through-holes extending from a first surface of the cuboid body to a second surface of the cuboid body, wherein the linear pattern of the plurality of through-holes is located at another end of the cuboid body.

2. The center of rotation guide of claim 1, wherein the at least one protuberance consists of one or more spikes or tines.

3. The center of rotation guide of claim 2, wherein the at least one protuberance consists of two spikes, and wherein one of the two spikes has a height of about 9 mm, and the other of the two spikes has a height of about 5 mm.

4. The center of rotation guide of claim 1, wherein the two or more concentric circular holes are through-holes extending from the first surface of the cuboid body to the second surface of the cuboid body, and wherein the two or more concentric circular holes determine the center of rotation of a lateral or medial epicondyle of the elbow.

5. The center of rotation guide of claim 1, wherein the linear pattern of the plurality of through-holes is positioned along a longitudinal axis of the cuboid body.

6. The center of rotation guide of claim 1, wherein the linear pattern of the plurality of through-holes is configured to identify an attachment point on an ulnar tuberosity.

7. The center of rotation guide of claim 1, wherein the length is about 1.9 to about 2.25 inches, the width is about 0.8 to about 1.2 inches, and the height is about 0.060 to 0.120 inches.

8. The center of rotation guide of claim 1, wherein the length is about 1.98 inches and the width is about 0.9 inches.

9. The center of rotation guide of claim 1, wherein the plurality of linear through-holes are symmetrically located relative to a longitudinal axis of the cuboid body.

10. The center of rotation guide of claim 1, wherein the guide is configured to be employed in ulnar collateral ligament repair or reconstruction.

11. The center of rotation guide of claim 1, wherein the guide is configured to be employed in lateral ulnar collateral ligament repair or reconstruction.

12. The center of rotation guide of claim 1, wherein the two or more concentric circular holes include a plurality of bisecting lines.

13. A surgical kit, comprising:
a center of rotation guide comprising a cuboid body; one or more spikes configured to attach to a surface of a capitellum to be drilled; two or more concentric circular holes of different diameters positioned at one end of the cuboid body for identifying a center of rotation of lateral or medial epicondyle, the two or more concentric circular holes including a plurality of bisecting lines; and a plurality of through-holes positioned at another end of the cuboid body for identifying an attachment point on ulnar tuberosity; and
at least one surgical instrument.

14. The surgical kit of claim 13, wherein the at least one surgical instrument is a pin, a guide, a k-wire, a drill, or a cutting instrument.

15. The surgical kit of claim 13, further comprising at least one fixation device.

16. The surgical kit of claim 15, wherein the at least one fixation device is a suture anchor.

17. The surgical kit of claim 13, wherein the center of rotation guide is disposable.

18. The surgical kit of claim 13, wherein the plurality of through-holes are symmetrically located relative to a longitudinal axis of the cuboid body.

* * * * *